United States Patent
Chu et al.

[11] Patent Number: 5,810,744
[45] Date of Patent: Sep. 22, 1998

[54] INSTRUMENT FOR COLLECTING MULTIPLE BIOPSY SPECIMENS

[75] Inventors: Michael S.H. Chu, Brookline; Yem Chin, Burlington, both of Mass.

[73] Assignee: Boston Scientific Corporation, Natick, Mass.

[21] Appl. No.: 972,174

[22] Filed: Nov. 18, 1997

Related U.S. Application Data

[63] Continuation of Ser. No. 608,047, Feb. 28, 1996, abandoned, which is a continuation of Ser. No. 428,280, Apr. 25, 1995, abandoned, which is a continuation of Ser. No. 62,671, May 17, 1993, abandoned.

[51] Int. Cl.⁶ ........................................................ A61B 5/00
[52] U.S. Cl. ................................................................ 600/567
[58] Field of Search ............................ 600/562, 564–567; 606/167, 170

[56] References Cited

U.S. PATENT DOCUMENTS

| | | | |
|---|---|---|---|
| 1,867,624 | 7/1932 | Hoffman | 128/754 |
| 2,541,542 | 12/1946 | Perez et al. | 128/754 |
| 2,850,007 | 9/1958 | Lingley | 128/2 |
| 3,001,522 | 9/1961 | Silverman | 128/754 |
| 3,147,749 | 9/1964 | Marsh | 128/751 |
| 3,175,554 | 3/1965 | Stewart | 128/754 |
| 3,342,175 | 9/1967 | Bulloch | 128/754 |
| 3,590,808 | 7/1971 | Muller | 128/2 |
| 3,606,878 | 9/1971 | Kellogg, Jr. | 128/2 |
| 3,692,020 | 9/1972 | Schied . | |
| 3,902,498 | 9/1975 | Niederer . | |
| 3,903,892 | 9/1975 | Komiya . | |
| 3,924,608 | 12/1975 | Mitsui | 128/751 X |
| 3,989,033 | 11/1976 | Halpern et al. . | |
| 4,007,732 | 2/1977 | Kvavle et al. | 128/2 |
| 4,020,847 | 5/1977 | Clark, III . | |
| 4,168,698 | 9/1979 | Ostergard | 128/751 |
| 4,178,810 | 12/1979 | Takahashi | 128/751 |
| 4,200,111 | 4/1980 | Harris | 128/751 |
| 4,220,155 | 9/1980 | Kimberling et al. | 128/306 |
| 4,243,048 | 1/1981 | Griffin | 128/751 |
| 4,282,884 | 8/1981 | Boebel | 128/754 |
| 4,393,872 | 7/1983 | Reznik et al. | 604/151 |
| 4,427,014 | 1/1984 | Bel et al. | 128/751 |
| 4,522,206 | 6/1985 | Whipple et al. | 128/752 |
| 4,574,803 | 3/1986 | Storz . | |
| 4,620,547 | 11/1986 | Boebel | 128/754 |
| 4,651,752 | 3/1987 | Fuerst | 128/754 |
| 4,651,753 | 3/1987 | Lifton | 128/751 |
| 4,662,371 | 5/1987 | Whipple et al. | 604/22 |
| 4,682,606 | 7/1987 | DeCaprio | 128/754 |

(List continued on next page.)

FOREIGN PATENT DOCUMENTS

| 2 479 680 | 4/1980 | France . |
| WO 93/04630 | 3/1993 | WIPO . |

OTHER PUBLICATIONS

Microvasive, "Steerable Catheter System" pp. 1–2, revised Jun. 1985.

*Primary Examiner*—Max Hindenburg
*Attorney, Agent, or Firm*—Finnegan, Henderson, Farabow, Garrett, & Dunner, L.L.P.

[57] ABSTRACT

The invention features a medical biopsy instrument including a relatively long shaft having proximal and distal ends, a biopsy assembly, located at the distal end of the shaft, an actuator located at the proximal end of the shaft, and a force-transmitting member associated with the shaft and extending from the actuator to the biopsy assembly. The biopsy assembly is constructed to receive tissue in a biopsy space and store severed tissue in a storage space. When collecting biopsy specimens, the biopsy assembly severs tissue located in the biopsy space and thereafter stores the severed tissue in the storage space. The storage space is arranged to store sequentially multiple severed biopsy specimens taken by multiple repeated actuations of the biopsy assembly. The biopsy assembly has a side cutting or a forward cutting embodiment and may be mounted of a catheter.

20 Claims, 6 Drawing Sheets

U.S. PATENT DOCUMENTS

| | | | |
|---|---|---|---|
| 4,693,257 | 9/1987 | Markham | 128/754 |
| 4,708,147 | 11/1987 | Haaga | 128/754 |
| 4,712,550 | 12/1987 | Sinnett | 128/334 |
| 4,721,116 | 1/1988 | Schintgen et al. | 128/751 |
| 4,733,662 | 3/1988 | DeSatnick et al. | 128/305 |
| 4,735,215 | 4/1988 | Goto et al. | 128/754 |
| 4,763,667 | 8/1988 | Manzo | 128/754 |
| 4,766,907 | 8/1988 | de Groot et al. | 128/754 |
| 4,776,346 | 10/1988 | Dan Baraha et al. | 128/754 |
| 4,785,826 | 11/1988 | Ward | 128/754 |
| 4,790,329 | 12/1988 | Simon | 128/749 |
| 4,799,495 | 1/1989 | Hawkins et al. | 128/754 |
| 4,817,630 | 4/1989 | Schintgen et al. | 128/751 |
| 4,867,156 | 9/1989 | Stack et al. | 128/754 |
| 4,881,550 | 11/1989 | Kothe | 128/752 |
| 4,887,612 | 12/1989 | Esser et al. | 128/751 |
| 4,893,635 | 1/1990 | de Groot et al. | 128/754 |
| 4,909,782 | 3/1990 | Semm et al. | 606/171 |
| 4,917,100 | 4/1990 | Nottke | 128/749 |
| 4,926,877 | 5/1990 | Bookwalter | 128/754 |
| 4,936,845 | 6/1990 | Stevens | 606/159 |
| 4,953,559 | 9/1990 | Salerno | 128/754 |
| 4,958,625 | 9/1990 | Bates et al. | 128/754 |
| 4,971,067 | 11/1990 | Bolduc et al. | 128/751 |
| 4,976,269 | 12/1990 | Mehl | 128/754 |
| 4,986,825 | 1/1991 | Bays et al. | 128/751 |
| 5,031,634 | 7/1991 | Simon | 128/754 |
| 5,056,529 | 10/1991 | de Groot | 128/754 |
| 5,074,311 | 12/1991 | Hasson | 128/754 |
| 5,082,000 | 1/1992 | Picha et al. | 128/751 |
| 5,085,658 | 2/1992 | Meyer | 606/46 |
| 5,085,659 | 2/1992 | Rydell | 606/47 |
| 5,133,360 | 7/1992 | Spears | 128/754 |
| 5,133,727 | 7/1992 | Bales et al. | 128/751 |
| 5,148,813 | 9/1992 | Bucalo | 128/754 |
| 5,156,160 | 10/1992 | Bennett | 128/754 |
| 5,171,255 | 12/1992 | Rydell | 606/170 |
| 5,172,700 | 12/1992 | Bencini et al. | 128/751 |
| 5,195,533 | 3/1993 | Yem Chin et al. | 128/754 |
| 5,211,655 | 5/1993 | Hasson | 128/751 |
| 5,217,458 | 6/1993 | Parins | 606/48 |
| 5,217,468 | 6/1993 | Clement | 606/127 |
| 5,224,488 | 7/1993 | Neuffer | 128/751 |
| 5,228,451 | 7/1993 | Bales et al. | 128/751 |
| 5,234,000 | 8/1993 | Hakky et al. | 128/754 |
| 5,242,461 | 9/1993 | Kortenbach et al. | 606/159 |
| 5,251,641 | 10/1993 | Xavier | 128/754 |
| 5,269,785 | 12/1993 | Bonutti | 606/80 |
| 5,281,230 | 1/1994 | Heidmueller | 606/127 |
| 5,331,971 | 7/1994 | Bales et al. | 128/749 |
| 5,334,198 | 8/1994 | Hart et al. | 606/52 |
| 5,342,390 | 8/1994 | Slater et al. | 128/749 |
| 5,375,608 | 12/1994 | Tiefenbrun et al. | 128/754 |
| 5,383,471 | 1/1995 | Funnell | 128/751 |
| 5,394,887 | 3/1995 | Haaga | 128/749 |
| 5,542,432 | 8/1996 | Slater et al. | 606/751 |

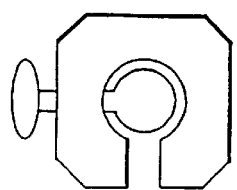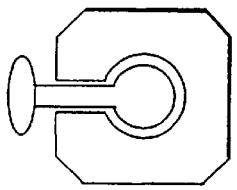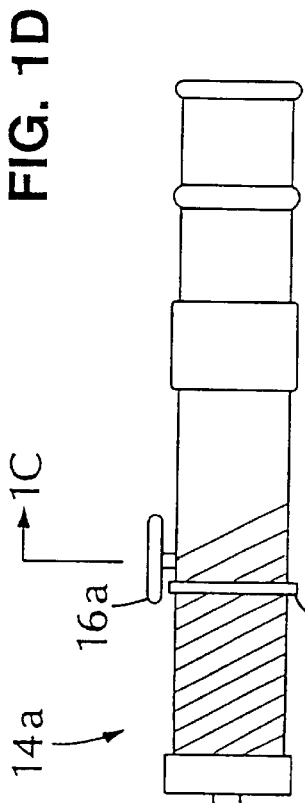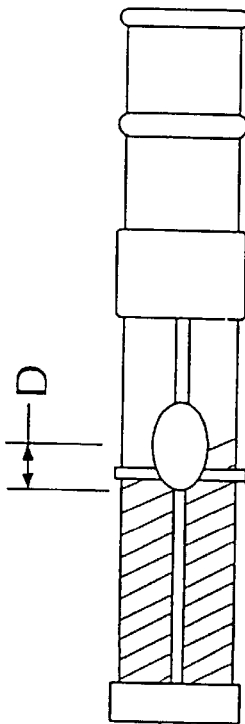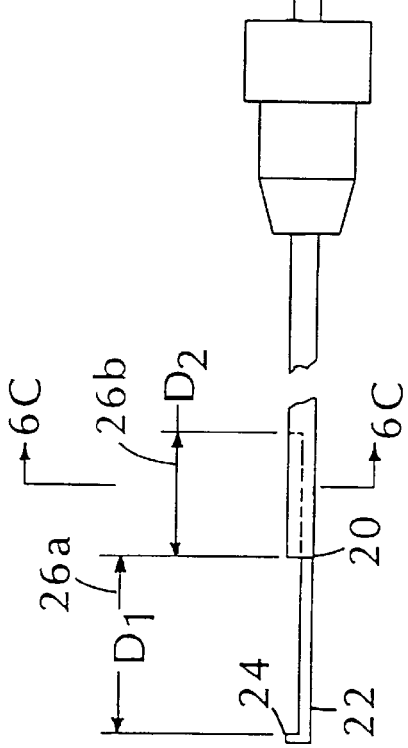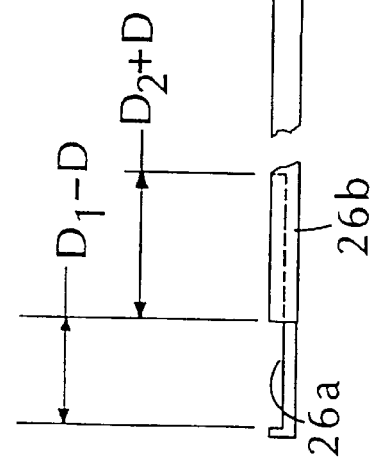

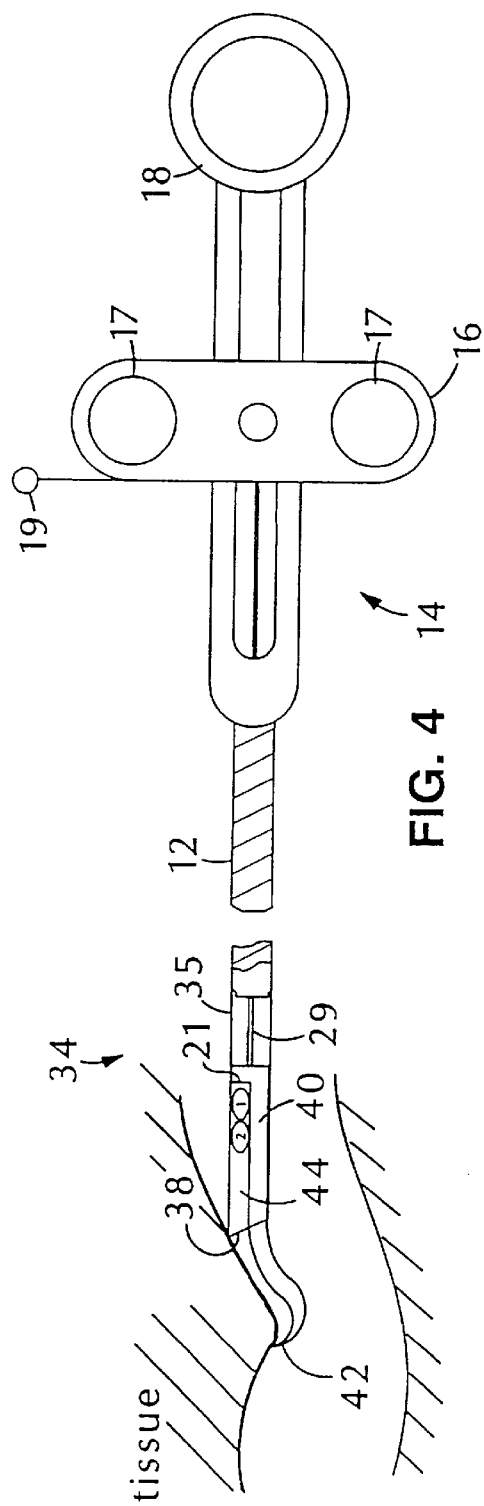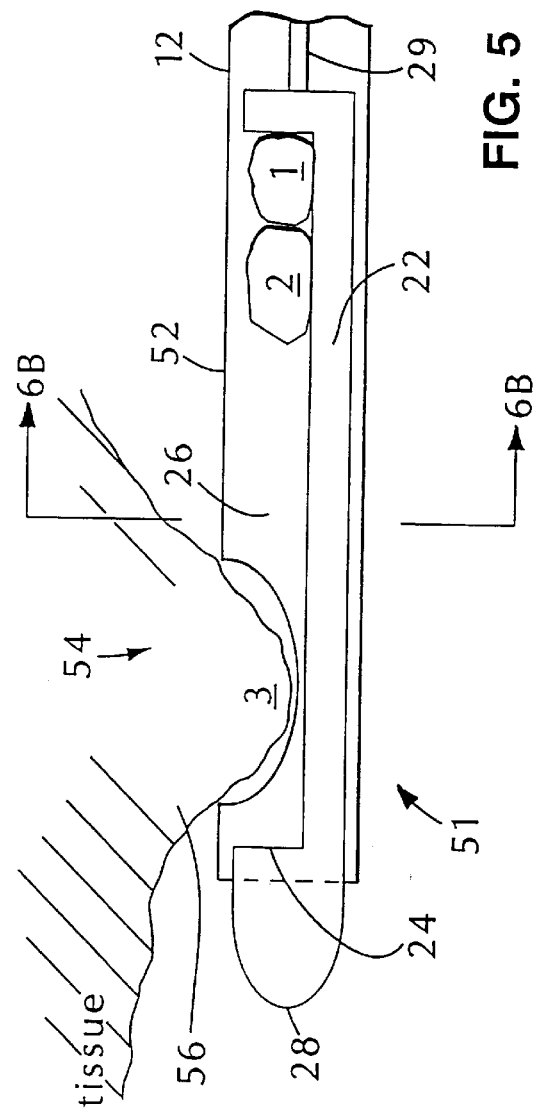

ND FOR COLLECTING
INSTRUMENT FOR COLLECTING
MULTIPLE BIOPSY SPECIMENS

This application is a continuation, of application Ser. No. 08/608,047, filed Feb. 28, 1996, now abandoned; which is a continuation of application Ser. No. 08/428,280, filed Apr. 25, 1995, now abandoned; which is a continuation of Ser. No. 08/062,671, filed May 17, 1993, now abandoned.

BACKGROUND OF THE INVENTION

This invention relates to biopsy instruments for collecting multiple biopsy specimens.

Presently, several biopsy techniques (e.g., pinch biopsy, snare excision biopsy, needle biopsy, suction biopsy) are used to obtain a biopsy specimen.

In general, a pinch biopsy is performed by a biopsy instrument having forceps with two jaws activated by a tension cord. The instrument is passed through an endoscope to a desired location and then the jaws are closed to grab and sever the biopsy sample. The instrument with the detached specimen is then withdrawn from the endoscope so that the tissue is removed. If another biopsy specimen is needed, the forceps are then re-inserted into the endoscope and relocated for the next biopsy. Frequently, due to a small moment arm of the instrument, the cutting force of the jaws is not sufficient or the jaws are not sharp enough to cleanly shear the tissue which is then torn off by a pulling movement.

A snare excision is performed with a distal hoop device passed through an endoscope. The tissue of interest is snared with the hoop which is then tightened to cut the tissue off. To remove the severed specimen, the hoop has to be withdrawn or an additional device for transporting the specimen is required.

A suction biopsy is usually performed with a single lumen flexible tube with a movable shearing device located therein. The tube having one or more portholes is passed through an endoscope, and the porthole is located at the desired tissue region. Next, suction is applied to the tube to pull the tissue inside the tube. The shearing device having its cutting edge guided along the inner wall of the tube is moved across the porthole to sever the tissue that is subsequently sucked into the tube. The severed specimen may be transported in the tube's lumen to a collection chamber located outside of the body.

To collect cells for cytological examination, a distal brush device is passed through an endoscope to a collection site. The brush is extended from its sheath and, by brushing the tissue, the cells are collected onto the bristles. The brush is retracted into the sheath to prevent decontamination, the instrument is withdrawn from the body, and the cells are deposited in a fixative system. However, the brush can collect only tissue cells which is often not sufficient since for many histopathological evaluations tissue samples are required.

A biopsy needle instrument has a long, thin stylet close-fitted within a cannula, and a firing device that first projects the stylet into the tissue and immediately thereafter projects the cannula. The stylet has a notch into which the tissue prolapses and is subsequently severed by the moving cannula. The biopsy instrument is then typically withdrawn, and the biopsy tissue is removed from the stylet.

In many situations, it is desirable to collect multiple biopsy specimens from the same location or several precisely defined locations. For example, when examining the spread of the diseased tissue, multiple biopsies are taken from several sites spread apart. In this process, if a biopsy instrument capable of collecting only a single specimen is used, the instrument must be withdrawn from the patient to remove the collected biopsy specimen before the next specimen can be taken; this substantially lengthens the biopsy process. For a subsequent biopsy, the physician has to re-insert and re-orient the biopsy instrument in relation to the previous biopsy site. The re-orientation may be quite difficult and time consuming since the biopsy instruments are often 200 cm. The time delay may cause a fatigue of the medical team, requires a longer sedation time of the patient and could also negatively affect the number and quality of the specimens which, in turn, could negatively influence the diagnosis.

SUMMARY OF THE INVENTION

In one aspect, the invention features a method and instrument for obtaining multiple biopsy specimens of different sizes. The instrument has a relatively simple mechanism and a small profile enabling frontal sampling or side sampling, for example, inside of blood vessels, gastrointestinal, urinary, respiratory, genital tract, inside of an organ, or at an organ's surface. The biopsy instrument includes a tubular cannula member attached to a rigid or a flexible shaft connected to a first segment of a two segment handle. The second segment of the handle, relatively movable with respect to the first segment, is connected to an inner receptacle member via a force transmitting member (e.g., a wire or a rod). The inner receptacle member, slidably fitted inside the cannula member, includes a biopsy groove adapted to store several biopsy samples. Only when the storage compartment is filled, the removal procedure of the biopsy specimen must be implemented.

The instrument has a forward shearing embodiment or a side shearing embodiment. In each embodiment, the instrument is constructed to have either a movable inner receptacle member or a movable cannula. If it is necessary to precisely target a surface of the biopsied tissue, it is preferable to use the second embodiment, wherein an edge of the inner receptacle member is held at the targeted tissue and the moving cannula severs the tissue. The distal end of the inner receptacle member may also include a sharp tip or a hook used to anchor the receptacle member in place during the shearing process. Alternatively, the distal end of the inner receptacle member may have a needle for insertion into tissue to take depth biopsies.

The shaft of the instrument may be rigid or flexible and is made in various lengths depending on the location of the targeted tissue. The specimens are severed by a compressive shearing action caused by moving the two pieces of the handle with respect to each other to create the force between the cutting edge of the cannula and the biopsy edge of the inner receptacle member.

In another aspect, the invention features a medical biopsy instrument including a relatively long shaft having proximal and distal ends, a biopsy assembly, located at the distal end of the shaft, constructed to receive tissue in a biopsy space and store severed tissue in a storage space, and an actuator located at the proximal end of the shaft. A force-transmitting member, associated with the shaft, extends from the actuator to the biopsy assembly that is constructed to sever tissue located in the biopsy space and thereafter store the severed tissue in the storage space. The storage space is arranged to store sequentially multiple severed biopsy specimens taken by multiple repeated actuations of the biopsy assembly.

Preferred embodiments of this aspect may include one or more of the following features.

The biopsy assembly includes a hollow cannula and an inner receptacle member, axially located in the cannula, arranged to form the biopsy space and the storage space, the cannula and the inner receptacle member constructed and arranged to move with respect to each other in order to shear, upon driving the actuator, the biopsy tissue located in the biopsy space and moving the severed tissue for storage in the receptacle member next to a previously stored biopsy tissue.

The inner receptacle member includes a member having a side groove and a side-facing biopsy edge, and the cannula includes a cutting edge located at its distal end. The cutting edge, the side groove, and the biopsy edge are arranged to form a side-facing arrangement of the biopsy space.

The biopsy assembly with the side-facing biopsy space is constructed to move, when driven by the actuator, either the cannula with respect to the inner receptacle member or the inner receptacle member with respect to the cannula to sever biopsy tissue.

The edge of the cannula is sharpened for improved cutting of the biopsy specimen.

The inner receptacle member includes a member having a groove and a biopsy edge at its distal end, and the cannula includes a cutting edge located at its distal end. The cutting edge, the groove, and the biopsy edge are arranged to form a forward-facing arrangement of the biopsy space.

The biopsy assembly with the forward-facing biopsy space is constructed to move, when driven by the actuator, the cannula with respect to the inner receptacle member or the inner receptacle member with respect to the cannula to sever biopsy tissue.

The inner receptacle member when extended from the cannula member assumes a preshaped bend adapted for a selected size of the biopsy specimen.

The shaft may be flexible or rigid. The flexible shaft together with the biopsy assembly are sized and constructed to pass through an extended narrow passageway. The rigid shaft together with the biopsy assembly are sized and constructed to pass through a passageway of interest. The flexible shaft is formed by a body of a catheter. The passage way may be a working channel of an endoscope.

The distal end of the inner receptacle member may further include a hook, a needle or a scalpel.

The biopsy instrument is used for surface biopsies or depth biopsies. For depth biopsies, the distal end may be further arranged to penetrate surface tissue and position the biopsy space at a deep seated tissue.

The actuator further includes a handle with a moving piece connected to the force transmitting member. The moving piece is constructed and arranged to facilitate driving of the actuator.

The biopsy instrument may further include a movement limiting member (e.g., a pin, a nut) constructed and arranged to limit motion of the piece thereby limiting the relative motion of the inner receptacle member and the cannula.

BRIEF DESCRIPTION OF THE DRAWING

FIGS. 1A and 1B show a modified embodiment of FIG. 1 for taking biopsy specimens of different sizes; FIG. 1C is a cross-sectional view of a thumb handle and a "C" shaped nut in "open" position shown in FIG. 1A in the 1C—1C; and FIG. 1D shows the thumb handle and the "C" shaped nut in "closed" position.

FIG. 2D is a cross-sectional view of the biopsy instrument of FIG. 2B in the 2D—2D direction.

FIG. 4 is a cross-sectional view of a biopsy instrument in accordance with another preferred embodiment of the present invention.

FIG. 5 is a cross-sectional view of a biopsy instrument in accordance with another preferred embodiment of the present invention.

DESCRIPTION OF THE PREFERRED EMBODIMENTS

Figure 1:
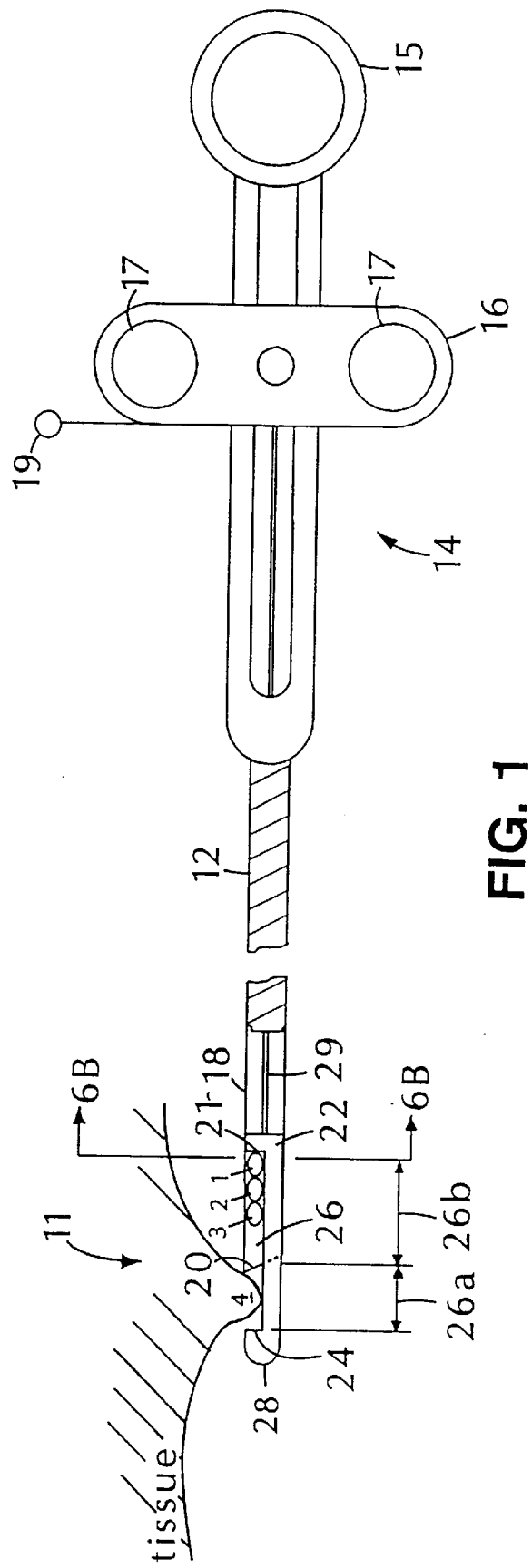
FIG. 1 is a cross-sectional view of a biopsy instrument in accordance with a first preferred embodiment of the present invention.

FIG. 1 shows a side shearing embodiment of a surface biopsy instrument taking a fourth biopsy specimen while three previously obtained specimens are stored inside of the instrument. The biopsy instrument includes a biopsy device 11, a shaft 12 made of a flexible metal coil sheath connected at its proximal end to an instrument handle 14 that consists of two parts axially movable with respect to each other. The first part includes a finger handle 16 with two finger rings 17 adapted for easy manipulation and the second part includes a thumb ring 15. The distal end of shaft 12 is connected to a proximal end of a cannula 18. The distal end of cannula 18 has a cannula edge 20. The lumen of cannula 18 and shaft 12 movably supports, in a close fit, an inner receptacle member 22 with its proximal end connected to a distal end of a force transmitting member 29 made of a wire. The proximal end of force transmitting member 29 is connected to finger handle 16. Inner receptacle member 22 includes a biopsy edge 24, a receptacle groove 26 formed along the longitudinal axis, and a round tip 28 located at its distal end. Receptacle groove 26 has two portions, i.e., exposed biopsy space 26a and enclosed storage space 26b; lengths of these portions vary and are determined by the position of receptacle member 22 in relation to cannula 18.

In this embodiment, inner receptacle member 22, force transmitting member 29 and finger handle 16 are adapted to slide with respect to shaft 12 and cannula 18. Handle 14 includes a slide that enables the movement of finger handle 16 from its proximal position at thumb ring 15 to its distal position at a release pin 19. This movement facilitates the extension of inner receptacle member 22 from a fully retracted position to a fully extended position. By moving release pin 19 to a different position on handle 14, finger handle 16 can slide over a different length thus varying the extension of inner receptacle member 22, i.e., the lengths of biopsy and storage spaces. As release pin 19 is moved distally, biopsy space 26a (the distance from biopsy edge 24 to cannula edge 20) increases and storage space 26b (the distance from cannula edge 20 to groove edge 21) decreases . On the other hand, by moving pin 19 proximally storage space 26b is increased and biopsy space 26a is decreased.

A modified embodiment for taking biopsy specimens of different sizes is shown in FIGS. 1A and 1B. A threaded C-shaped nut 19a in cooperation with a threaded handle 14a replace release pin 19. When finger handle 16a is located at C-shaped nut 19a, inner receptacle member 22 is in an extended position having the distance from biopsy edge 24 to cannula edge 20 (cutting span $D_1$), while the span from cannula edge 20 to receptacle end 21 defines a closed storage space with a distance $D_2$. By moving C-shaped nut 19a proximally by a distance D, inner receptacle member 22 can now extend only over a shorter distance (i.e., $D_1$–D) resulting in a longer closed storage space (i.e., $D_2$+D).

Another equally important embodiment is constructed to move the cannula in respect to the inner receptacle member. Here, cannula 18 extends from a retracted position having receptacle groove 26 substantially exposed, to an extended position wherein cannula edge 20 is moved beyond biopsy edge 24 so that cannula 18 completely covers receptacle groove 26.

Shaft 12 is made either of a relatively flexible material or a rigid material. The flexible material (e.g., a coil sheath, a thin wall hypotubing, laminated structures having a braided steel mesh, or teflon™) is designed to be flexible and yet torqueable and capable to bear a compressive load so that the biopsy instrument can be maneuvered into place. Shaft 12 is made in various lengths depending on the location of the targeted tissue.

Figure 2A:
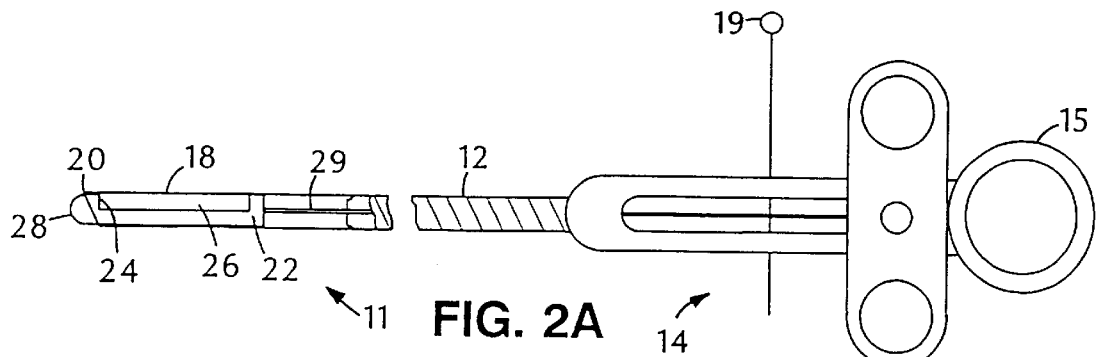
FIGS. 2A, 2B, 2C depict the operation of the biopsy instrument of FIG. 1 taking a first specimen.
Figure 2B:
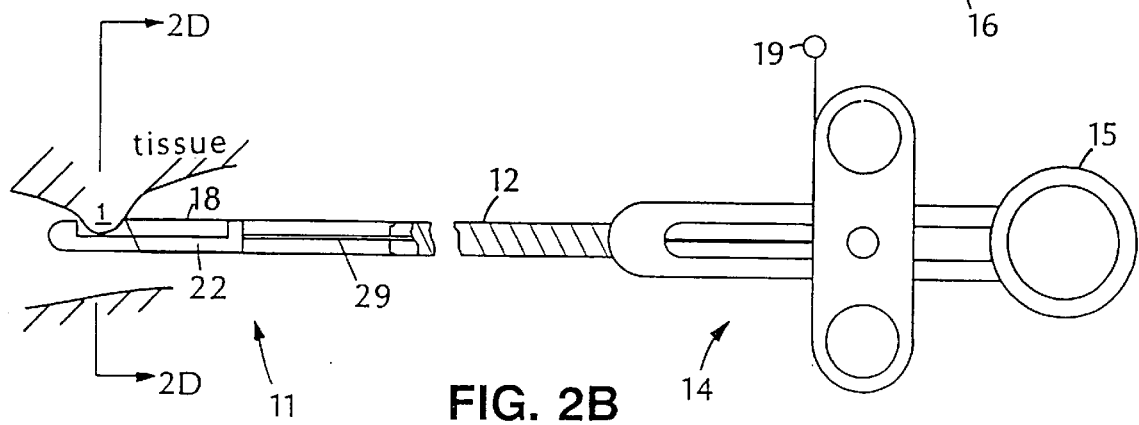
Figure 2C:
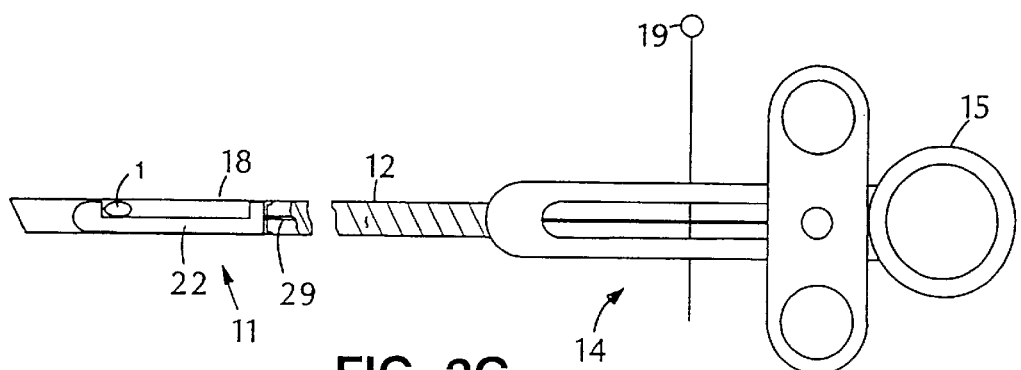

Referring to FIG. 2A, when inserted into a body lumen, the biopsy instrument has only round tip 26 exposed; this protects tissue (or endoscope surfaces if an endoscope is used to introduce the instrument) from the sharpened cannula edge 20 or biopsy edge 24. Once a biopsy site is located, finger handle 16 is pushed distally to expose tissue to a predetermined cutting distance. (FIG. 2B). The cutting distance is adjusted by positioning pin 19 at a desired location on handle 14. A portion of the tissue prolapses into the biopsy space between biopsy edge 24 and cannula edge 20. To slice this tissue off, finger handle 16 is pulled proximally towards thumb ring 15 causing retraction of inner receptacle member 22 and thereby shearing of the tissue by cannula edge 20 of the stationary cannula. The severed tissue is encapsulated in storage space 26b. Further motion of finger handle 16 moves the severed tissue restrained by biopsy edge 24 inside of the cannula lumen until finger handle 16 comes to rest at thumb ring 15 (FIG. 2C).

Figure 3A:
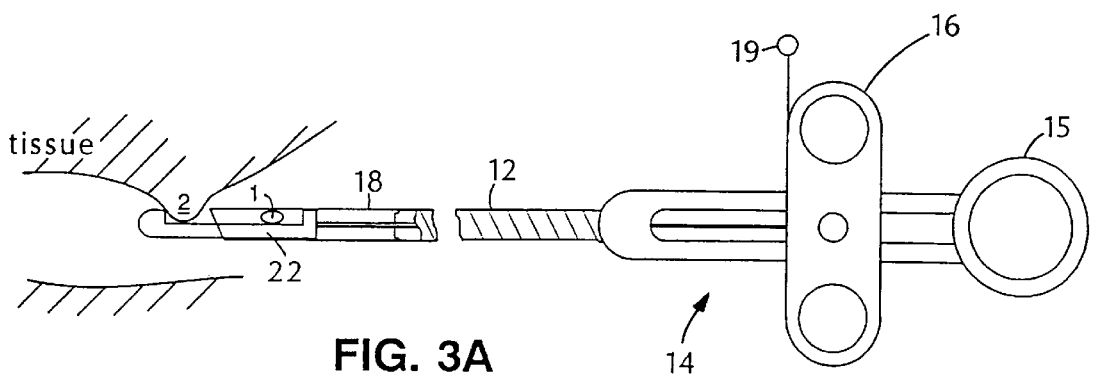
FIG. 3A, 3B, 3C depict the operation of the biopsy instrument of FIG. 1 taking a second and a third specimen.

Referring to FIG. 3A, without removing the collected specimen, a second biopsy site is located. To collect a second biopsy specimen, finger handle 16 is pushed distally to expose a predetermined distance of biopsy space 26a. Due to a much greater friction force on the inner surface of cannula 18 than on the surface of storage space 26b, the first specimen remains well within the lumen of cannula 18. The surfaces in contact with the specimen may have a selected different finish designed to increase the friction on the inner surface of cannula 18 and decrease the friction on the surface of receptacle groove 26; however, this is not necessary for proper functioning of the instrument.

Figure 3B:
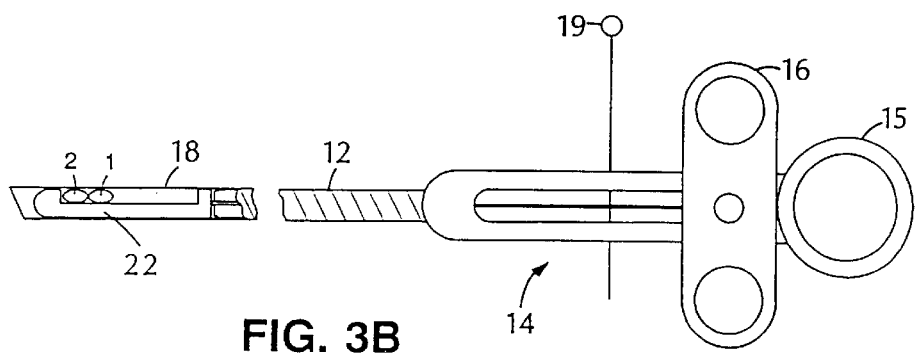
Figure 3C:
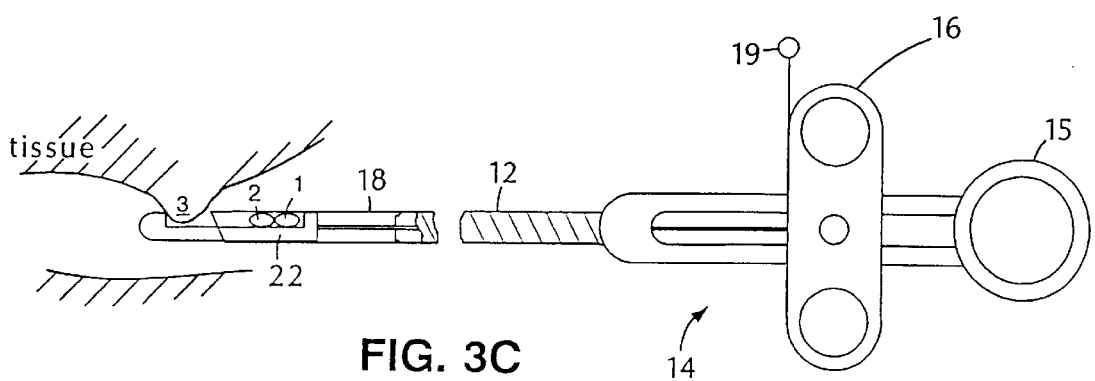
Figure 6A:
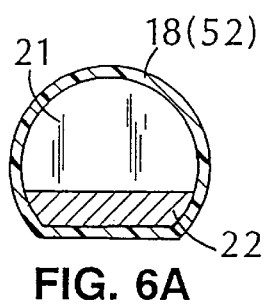
FIGS. 6A, 6B, 6C, 6D, 6E and 6F depict different shapes of the cutting edges of the above-pictured biopsy instruments shown in a cross-sectional view.
Figure 6B:
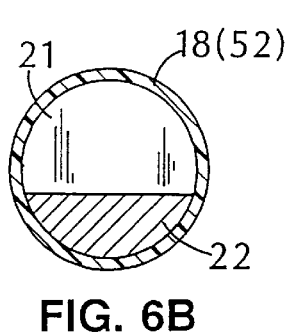
Figure 6C:
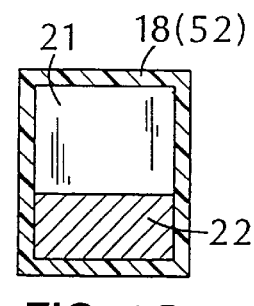
Figure 6D:
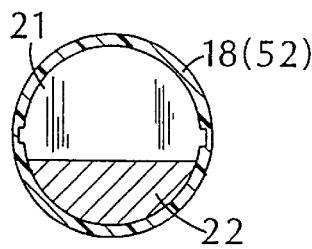
Figure 6E:
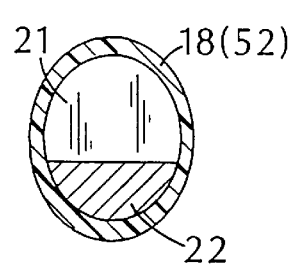
Figure 6F:
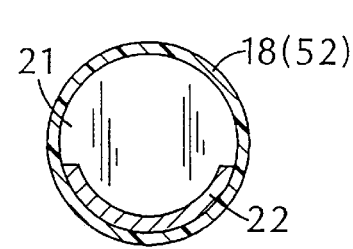

A second biopsy tissue prolapses into the biopsy space and the tissue is again sliced off by moving finger handle 16 towards thumb ring 15, as shown in FIG. 3B. In this retracting motion, the two specimens travel within storage space 26b inside the cannula, wherein due to the large friction on the inside surface of cannula 18, the second specimen adjoins the first one. Referring to FIG. 3C, a third and any subsequent biopsy specimen is taken in the same way as described above. For each subsequent biopsy, pin 19 may be moved to a different proximal position on handle 14 so that the length of the enclosed portion of receptacle 26, i.e., storage space 26b, is increased while the length of biopsy space 26a is decreased.

Another preferred embodiment of the present invention adapted for frontal biopsies is shown in FIG. 4. The biopsy instrument includes a cannula 35 mounted on the distal end of shaft 12. A cannula edge 38 located on the distal end of cannula 35 forms a relatively sharp angle with the axis of the cannula. An inner receptacle member 40, connected to force transmitting member 29, is bent at a 45° angle and terminated by a relatively sharp cutting edge 42. Inner receptacle member 40 is again adapted to be retracted inside of cannula 35 by moving finger handle 16 from its distal position at pin 19 to a proximal position of thumb ring 15. The distance between pin 19 and thumb ring 15, adjustable by moving pin 19 between several positions on handle 14, defines the size of the biopsy specimen. The space between receptacle member 40 and cannula 35 forms receptacle storage 44 for storing collected biopsy specimens. The biopsy instrument 34 can have again either a flexible shaft or a rigid shaft. In the first case the force transmitting member 29 is made of a wire, and in the second of a rod.

In another preferred embodiment of biopsy instrument 34, inner receptacle member 40 is stationary and cannula 35 is movable.

To perform biopsy using biopsy instrument 34, biopsy instrument 34 with its receptacle member 40 retracted is first introduced to a body lumen via an endoscope. After a biopsy site is located, finger handle 16 is pushed distally to extend inner receptacle member 40 from cannula 35 and to expose the biopsy jaws to surround the desired biopsy—tissue. To biopsy this tissue, finger handle 16 is moved proximally toward thumb ring 15 causing retraction of inner receptacle member 40 and shearing off the specimen. Biopsy edge 42 moves the severed tissue inside cannula 35. Without removing the specimen, a next biopsy site is located. Finger handle 16 is again pushed distally to a position limited by location of pin 19 that, in turn, defines the extension of receptacle member 40, i.e., opening of the biopsy jaw. As described for the side shearing embodiment of FIG. 1, the previous biopsy specimen remains inside of cannula 35 due to a relatively large friction force of the inside surface of cannula 35. Each surface may have a special finish to increase the friction on the inside surface of cannula 35 and decrease the friction on the receptacle surface. This embodiment again enables taking several subsequent biopsies in the same way as described above.

The size of the biopsy specimens can be affected either by changing the angle of deflection of the inner receptacle member with respect to the cannula, which is done during the manufacturing process, or just before taking biopsy by moving pin 19 to a different position on the handle to alter the relationship between the biopsy space and the storage space as described above.

In the above described embodiments, the specimens are removed from the instrument by removing pin 19 and pushing distally finger handle 16 to expose fully the receptacle groove. The specimens are then removed in a reverse sequential order from the order in which they were collected.

Referring to FIG. 5, in another embodiment of the biopsy instrument, a biopsy device 51 is constructed by replacing the cannula with a distal tubular member 52 connected to the distal end of shaft 12. Distal tubular member 52 has at least one side hole 54 located near its distal end and adapted to accept tissue 56 for a surface biopsy. The side hole portion of distal tubular member 52 is made of a steel (or other relatively hard material) and the outer edges of inner receptacle member 22 are fabricated in a close fit with the inner surface of distal tubular member 52 to achieve an even biopsy cut. FIGS. 6A through 6F are cross-sectional views of different shapes of inner receptacle member 22 and distal tubular member 52. (Note that the embodiment of FIG. 5 uses distal tubular member 52, shown in parentheses, instead of cannula 18.) Different cross-sections of the two members are selected to biopsy different tissue types of sizes, e.g., a biopsy instrument with the cross-section shown in FIG. 6F collects larger samples than an instrument with the cross-section shown in FIG. 6B.

In the biopsy process, the instrument is maneuvered and pressed with its side hole 54 at a tissue region of interest. After the tissue prolapses into side hole 54, tissue 56 is severed by moving inner receptacle member 22 beyond hole 54. FIG. 5 depicts two biopsy samples located in the storage portion and a third sample in side hole 54. The biopsy instrument may also be modified by adding a suction device connected to distal tubular member 52 to pull tissue into side hole 54; this improves the grip on some types of tissue before and during the shearing action of receptacle member 22.

The biopsy instruments of FIG. 1 or FIG. 4 may also include a hook or a sharp tip located at the distal end of the inner receptacle member that is used to anchor the receptacle member in place during the positioning of the instrument and the shearing process. Alternatively, the distal end of the inner receptacle member may form a needle adapted to take depth biopsies.

The receptacle groove may have a semi-circular shape, a V-shape or a 360° type cut for a side biopsy at any angle. The carriage release pin can be replaced by a chip of smaller profile. FIGS. 6A, 6B, 6C, 6D, 6E and 6F depict several possible shapes of the inner receptacle member and the cannula closely fitted to each other. The above-described individual embodiments offer different advantages depending on the type and location of the biopsied tissue.

Other embodiments are within the following claims:

We claim:

1. A forward-sampling instrument for obtaining multiple tissue samples from tissue sites within a body, comprising:
   a proximal portion that remains outside the body including an actuator with a force transmitting element extending from said actuator,
   a flexible, elongated catheter body portion constructed to follow a path to said tissue sites within the body, said force transmitting element extending through an interior of said catheter body portion, and
   a distal portion defining a central axis and including a storage space in which multiple biopsy samples are stored, said storage space located proximal to a forward-sampling cutter, said cutter having relatively moveable cutting elements constructed to receive tissue and sever samples from tissue sites in front of said cutter, said moveable cutting elements including a cutting element connected to said force-transmitting element, distally extendable at an angle transverse to the axis defined by the distal portion, and terminating in a cutting edge, said cutter being controlled with said actuator at said proximal portion by applying forces to said force-transmitting element so that movement of the cutting element in a proximal direction relative to the catheter body portion causes the cutting element to sever a tissue sample and move the tissue sample into the storage space, and said storage space being adjacent and proximal to said cutter for storing a succession of samples while further samples are severed by said cutter.

2. The instrument of claim 1 wherein said force transmitting element is a wire.

3. The instrument of claim 1 wherein said cutter includes a second cutting element extending parallel to said axis defined by the distal portion.

4. The instrument of claim 3 wherein said second cutting element is a tube.

5. The instrument of claim 4 wherein said cutting element extendable at an angle can be moved into and out of said tube.

6. The instrument of claim 5 wherein said cutting element extendable at an angle assumes a pre-shaped bend when moved out of said tube.

7. The instrument of claim 1 sized and constructed to pass through the working channel of an endoscope.

8. The instrument of claim 1 wherein the diameter of said storage space is sized to substantially correspond to the diameter of said samples.

9. The instrument of claim 1 wherein the angle of extension of said cutting member is constructed to control the size of said samples.

10. The instrument of claim 1 wherein said distal portion is constructed to permit retrieval of said samples from said storage space by extending said cutting element distally.

11. A method for obtaining multiple tissue samples from tissue sites within a body, comprising the steps of:
   providing a forward-sampling instrument having
   a proximal portion that remains outside the body including an actuator with a force transmitting element extending from said actuator,
   a flexible, elongated catheter-body portion constructed to follow a path to said tissue sites within the body, said force transmitting element extending through an interior of said catheter-body portion, and
   a distal portion defining a central axis including a storage space in which multiple biopsy samples are stored, said storage space located proximal to a forward-sampling cutter, said cutter having relatively moveable cutting elements constructed to receive tissue and sever samples from tissue sites in front of said cutter, said moveable cutting elements including a cutting element connected to said force-transmitting element, distally extendable at an angle transverse to the axis defined by the distal portion, and terminating in a cutting edge, said cutter being controlled with said actuator at said proximal portion by applying forces to said force-transmitting element, and said storage space being adjacent and proximal to said cutter for storing a succession of samples while further samples are severed by said cutter;
   maneuvering said forward-sampling instrument along said path to a tissue site in front of said cutter;
   extending said cutting element at an angle transverse to the axis defined by the distal portion by applying forces to said actuator which is transmitted by said force transmitting element extending through said catheter body to said cutter;
   moving the cutting element in a proximal direction relative to the catheter-body portion so that the cutting element severs a tissue sample from the tissue site and moves the tissue sample into the storage space by applying forces to said actuator which are transmitted by said force-transmitting element extending through said catheter body to said cutter,
   storing said sample in said storage space without removing said device from the body,
   repeating said maneuvering, severing, and storing steps, and
   removing said instrument from the body.

12. The method of claim 11 comprising removing said samples from said storage space by extending said cutting element distally to gain access to said storage space.

13. The method of claims 11 and 12 comprising:
passing said instrument along a path defined by the working channel of an endoscope.

14. The method of claim 11 wherein said force transmitting element is a wire.

15. The method of claim 11 wherein said cutter includes a second cutting element extending parallel to said axis defined by the distal portion.

16. The method of claim 15 wherein said second cutting element is a tube.

17. The method of claim 16 wherein said cutting element extendable at an angle can be moved into and out of said tube.

18. The method of claim 17 wherein said cutting element extendable at an angle assumes a pre-shaped bend when moved out of said tube.

19. The method of claim 11 wherein the diameter of said storage space is sized to substantially correspond to the diameter of said samples.

20. The method of claim 11 wherein the angle of extension of said cutting member is constructed to control the size of said samples.

* * * * *

UNITED STATES PATENT AND TRADEMARK OFFICE
CERTIFICATE OF CORRECTION

PATENT NO. : 5,810,744
DATED : September 22, 1998
INVENTOR(S) : Michael S.H. CHU et al.

It is certified that error appears in the above-indentified patent and that said Letters Patent is hereby corrected as shown below:

On the Title Page, Item [56] "References Cited," under "Foreign Patent Documents," please add --7,705,342         2/1977          Germany--.

Signed and Sealed this

Second Day of February, 1999

Attest:

Attesting Officer

*Acting Commissioner of Patents and Trademarks*